(12) United States Patent
Gobin et al.

(10) Patent No.: US 6,416,533 B1
(45) Date of Patent: Jul. 9, 2002

(54) INDWELLING HEAT EXCHANGE CATHETER AND METHOD OF USING SAME

(75) Inventors: Yves Pierre Gobin, Los Angeles; Scott M. Evans, Santa Ana; Michael Jones, Capistrano Beach; Wayne A. Noda, Mission Viejo, all of CA (US)

(73) Assignees: Alsius Corporation, Irvine; The Regents of the University of California, Berkeley, both of CA (US)

( * ) Notice: Subject to any disclaimer, the term of this patent is extended or adjusted under 35 U.S.C. 154(b) by 0 days.

(21) Appl. No.: 09/546,814

(22) Filed: Apr. 11, 2000

Related U.S. Application Data

(62) Division of application No. 09/063,984, filed on Apr. 21, 1998, now Pat. No. 6,126,684.

(51) Int. Cl.[7] .................................................. A61F 7/12
(52) U.S. Cl. ........................ 607/113; 607/106; 604/113
(58) Field of Search ................................ 607/104, 105, 607/106, 113, 107; 606/20–26; 604/113

(56) References Cited

U.S. PATENT DOCUMENTS

| | | |
|---|---|---|
| 2,058,780 A | 10/1936 | Elliot |
| 2,077,453 A | 4/1937 | Albright |
| 3,425,419 A | 2/1969 | Dato |
| 3,460,538 A | 8/1969 | Armstrong |
| 3,504,674 A | 4/1970 | Swenson et al. |
| 3,776,241 A | 12/1973 | Magilton |
| 3,897,790 A | 8/1975 | Magilton et al. |
| 4,111,209 A | 9/1978 | Wolvek |
| 4,181,132 A | 1/1980 | Parks |
| 4,707,587 A | 11/1987 | Greenblatt |
| 4,840,617 A | 6/1989 | Osterholm |

(List continued on next page.)

OTHER PUBLICATIONS

U.S. patent application Ser. No. 09/133,813, Noda et al., app. pending.
U.S. patent application Ser. No. 09/266,452 Evans et al., app. pending.
U.S. patent application Ser. No. 09/282,971, Philips, app. pending.
U.S. patent application Ser. No. 09/294,080, Walker et al., app. pending.
U.S. patent application Ser. No. 09/321,350, Walker, app. pending.
U.S. patent application Ser. No. 09/390,600, Luo et al., app. pending.
U.S. patent application Ser. No. 09/413,752, Evans et al., app. pending.
U.S. patent application Ser. No. 09/413,753, Evans et al., app. pending.
U.S. patent application Ser. No.09/427,745, Pham et al., app. pending.

(List continued on next page.)

*Primary Examiner*—Roy D. Gibson
(74) *Attorney, Agent, or Firm*—Arlyn Alonzo

(57) ABSTRACT

A catheter is adapted to exchange heat with a body fluid, such as blood, flowing in a body conduit, such as a blood vessel. The catheter includes a shaft with a heat exchange region disposed at its distal end. This region may include at least one balloon which is adapted to receive a remotely cooled heat exchange fluid preferably flowing in a direction counter to that of the body fluid. Embodiments including multiple balloons enhance the surface area of contact, and the mixing of both the heat exchange and the body fluid. The catheter can be positioned to produce hypothermia in a selective area of the body without cooling the entire body system. It is of particular advantage in brain surgeries where stroke, trauma or cryogenic tumors can best be addressed under hypothermic conditions.

19 Claims, 10 Drawing Sheets

U.S. PATENT DOCUMENTS

| | | | |
|---|---|---|---|
| 5,011,468 A | 4/1991 | Lundquist | |
| 5,059,167 A | 10/1991 | Lundquist | |
| 5,078,713 A | 1/1992 | Varney | |
| 5,149,321 A | 9/1992 | Klatz et al. | |
| 5,151,100 A | 9/1992 | Abele et al. | |
| 5,234,405 A | 8/1993 | Klatz et al. | |
| 5,383,856 A | 1/1995 | Bersin | |
| 5,395,314 A | 3/1995 | Klatz et al. | |
| 5,437,673 A | 8/1995 | Baust | |
| 5,486,204 A | 1/1996 | Clifton | |
| 5,486,208 A | 1/1996 | Ginsburg | |
| 5,549,559 A | 8/1996 | Eshel | |
| 5,609,591 A | 3/1997 | Daikuzono | |
| 5,624,392 A | 4/1997 | Saab | |
| 5,716,386 A | 2/1998 | Ward | |
| 5,837,003 A | 11/1998 | Ginsburg | |
| 5,879,316 A | 3/1999 | Safar et al. | |
| 5,899,899 A | * 5/1999 | Arless et al. | 606/22 |
| 5,902,299 A | 5/1999 | Jayaraman | |
| 5,906,588 A | 5/1999 | Safar et al. | |
| 5,916,242 A | * 6/1999 | Schwartz | 607/104 |
| 6,019,783 A | 2/2000 | Philips et al. | |
| 6,051,019 A | * 4/2000 | Dobak, III | 607/104 |
| 6,126,684 A | 10/2000 | Gobin et al. | |
| 6,146,411 A | 11/2000 | Noda et al. | |
| 6,231,594 C1 | 5/2001 | Dae | |

OTHER PUBLICATIONS

U.S. patent application Ser. No. 09/456,110, Luo et al., app. pending.

U.S. patent application Ser. No. 09/477,490, Lasersohn et al., app. pending.

U.S. patent application Ser. No. 09/503,014, Gobin et al., app. pending.

U.S. patent application Ser. No. 09/498,499, Worthen, app. pending.

U.S. patent application Ser. No. 09/540,693, Worthen et al., app. pending.

U.S. patent application Ser. No. 09/546,814, Gobin et al., app. pending.

U.S. patent application Ser. No. 09/565,039, Worthen et al., app. pending.

Bruder et al., Influence of body temperature, with or without sedation, on energy expenditure in severe head–injured patients, *Critical Care Medicine*, 1998 Mar. 26(3):568–572.

Dietrich, W., The Importance of Brain Temperature in Cerebral Injury, *Journal of Neurotrauma*, May 9, 1992(2):S475–S485.

Ginsberg et al., Therapeutic Modulation of Brain Temperature: Relevance to Ischemic Brain Injury, *Cerebrovascular and Brain Metabolism Reviews* 1992 Fall, 4(3):189–225.

Henker et al., Comparison of brain temperature with bladder and rectal temperatures in adults with severe head injuries, Neurosurgery, May 1998, 42(5):1071–1075.

Maher et al., Hypothermia as a potential treatment for a cerebral ischemia, *Cerebrovascular and Brain Metabolism Reviews*, 1993 Winter, 5(4):277–300.

Marion et al., Treatment of traumatic brain injury with moderate hypothermia, *The New England Journal of Medicine*, Feb. 1997, 336(8):540–546.

Ping et al., Protection of the Brain from Hypoxia: A Review, *Can Anaesth. Soc J,* Nov 25, 1978, (6):468–473.

Sessler, D., Deliberate Mild Hypothermia, *Journal of Neurosurgical Anesthesiology*, Jan. 7, 1995(1):38–46.

Smirnov, O.A., New Method for Cooling (or Heating) the Body and an Apparatus for Craniocerebral Hypothermia, *Biomed Eng.* Nov.–Dec. 1968, 2(6):334–347.

* cited by examiner

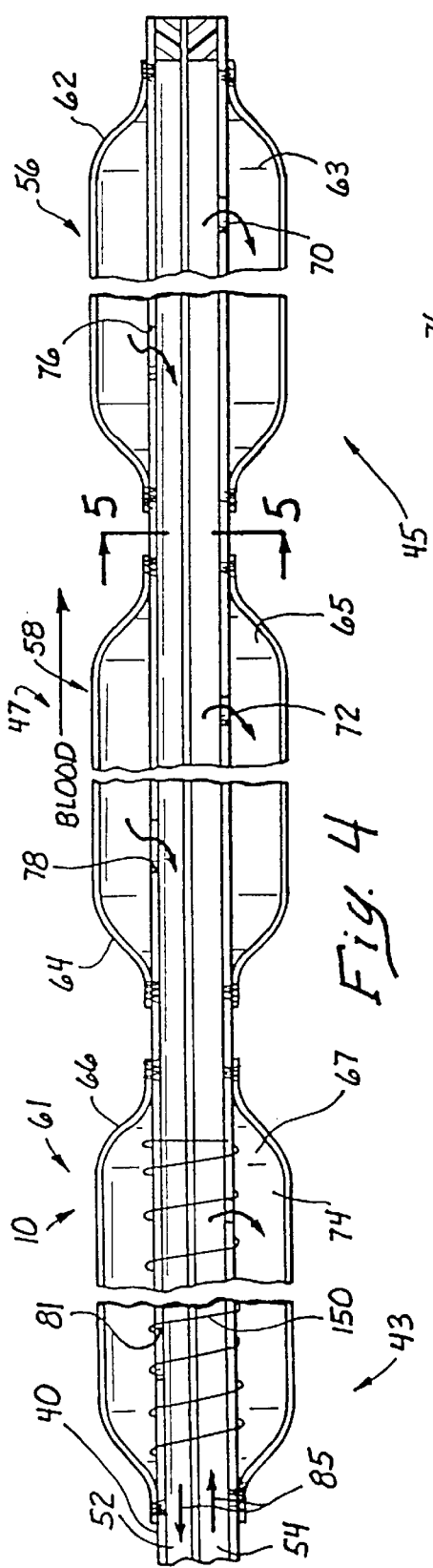
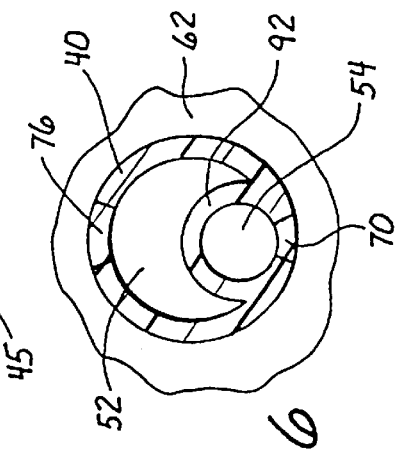
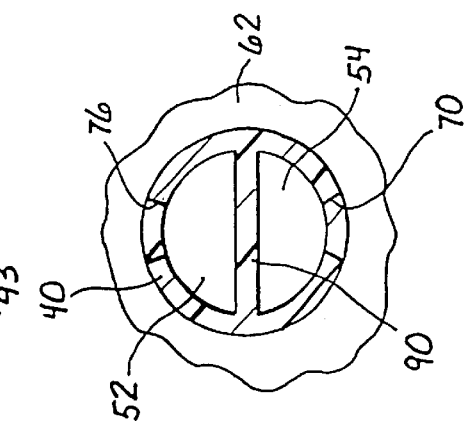

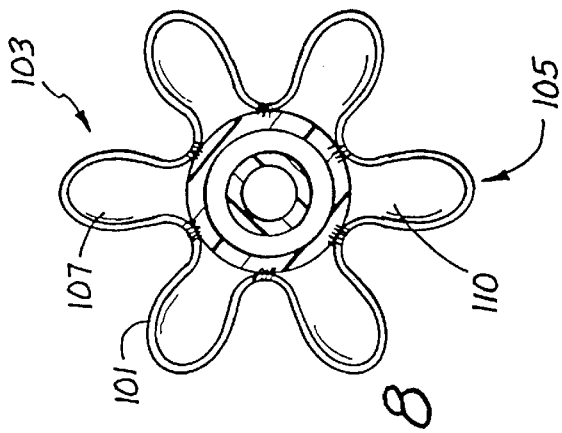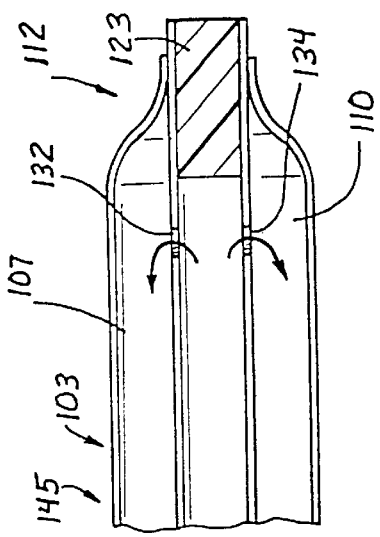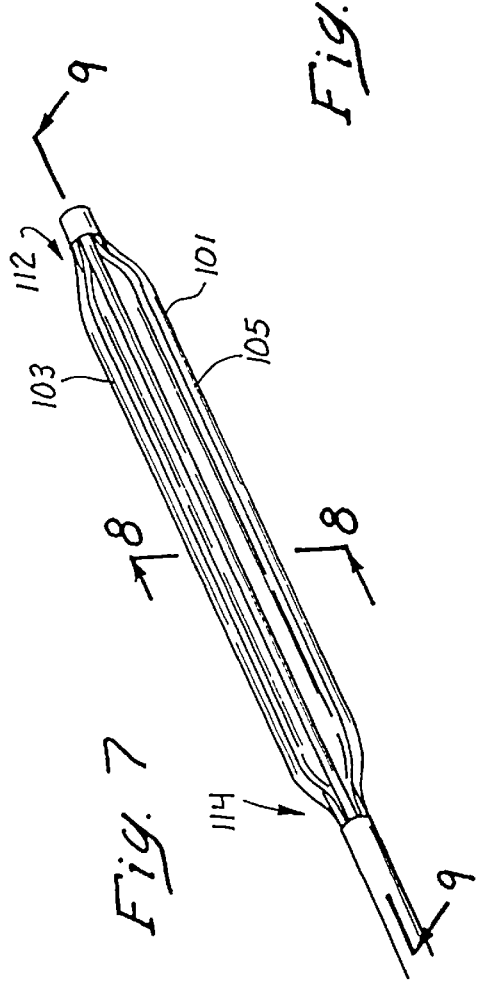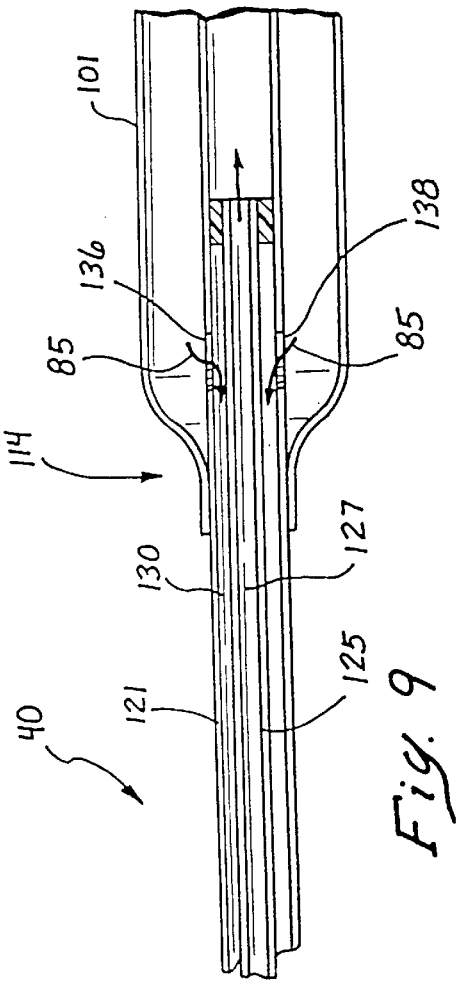

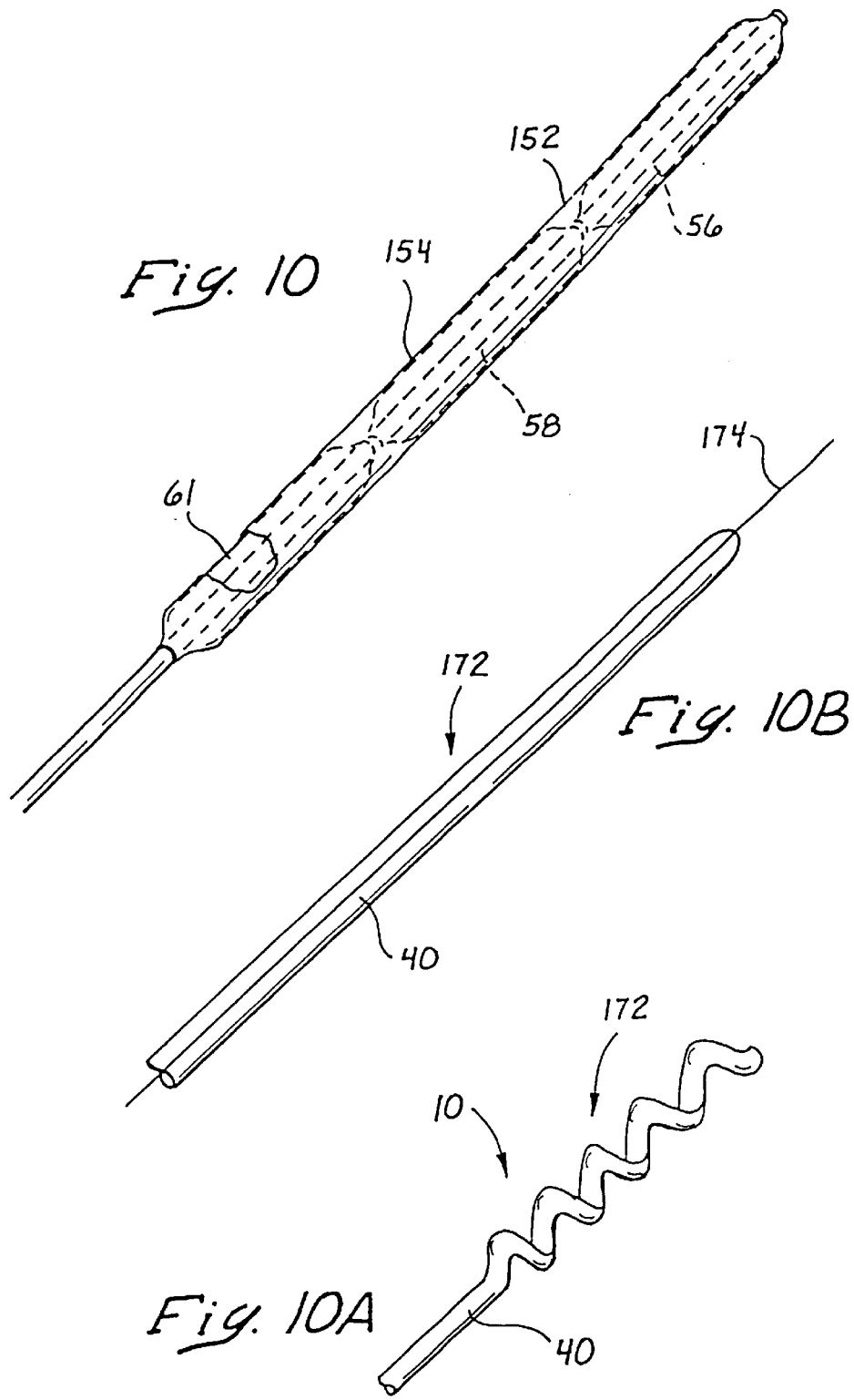

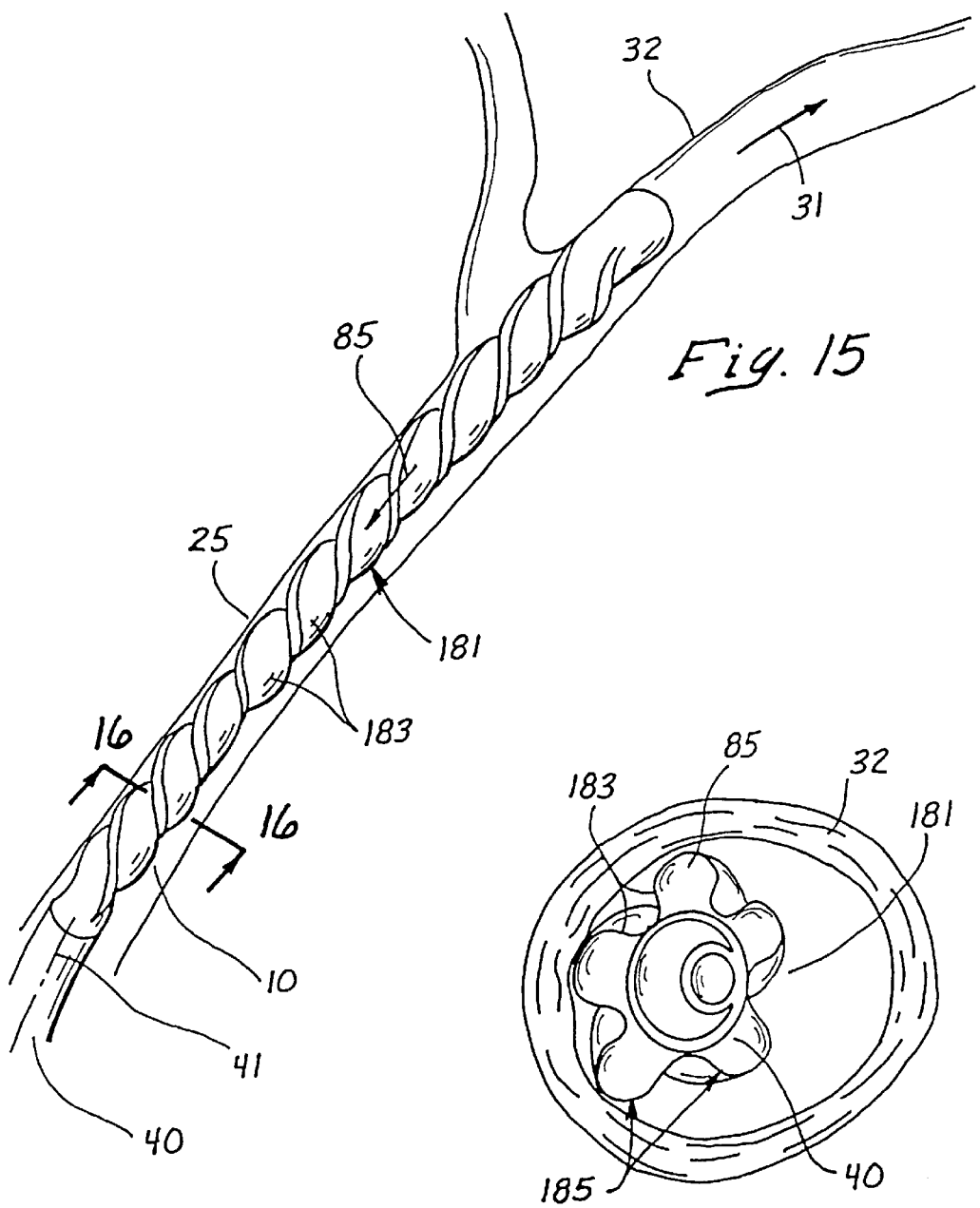

INDWELLING HEAT EXCHANGE CATHETER AND METHOD OF USING SAME

This application is a divisional of co-pending allowed patent application Ser. No. 09/063,984, filed on Apr. 21, 1998. Priority is claimed from patent application Ser. No. 09/063,984, now U.S. Pat. No. 6,126,684.

BACKGROUND OF THE INVENTION

1. Field of the Invention

This invention relates generally to apparatus and methods for producing heat exchange with body tissue, and more specifically to methods and apparatus for the hypothermic treatment of a body fluid in a body conduit.

2. Discussion of the Prior Art

Many of the advantages of hypothermia are well known. By way of example, it has been found particularly desirable to lower the temperature of body tissue in order to reduce the metabolism of the body. In stroke and several other pathological conditions, hypothermia also reduces the permeability of the blood/brain barrier. It inhibits release of damaging neurotransmitters and also inhibits calcium-mediated effects. Hypothermia inhibits brain edema and lowers intracranial pressure.

Some of the disadvantages of systemic hypothermia include cardiac arrhythmia, pulmonary edema and coagulopathies. Systemic hypothermia also results in hypotension and various immunodeficiencies.

In the past, hypothermic treatment has been addressed systemically, meaning that the overall temperature of the entire body has been lowered to achieve the advantages noted above. This has been particularly desirable in surgical applications where the reduced metabolism has made it possible to more easily accommodate lengthy operative procedures. An example of this systemic approach includes catheters for transferring heat to or from blood flowing within a patient's vessel, as disclosed by Ginsburg in U.S. Pat. No. 5,486,208. A closed loop heat exchange catheter is also disclosed by Saab in U.S. Pat. No. 5,624,392, The systemic approach is not always advantageous when the beneficial effects are desired locally at the focus of the operative procedure and only the disadvantages of hypothermia are felt throughout the remainder of the body.

As a result, more recent focus has been directed to producing hypothermia in localized areas of the body, leaving the remainder of the body to function at a normal body temperature. These localized applications of hypothermia have been external, relying for example on cooling helmets or cooling neck collars to produce localized hypothermia for the brain.

SUMMARY OF THE INVENTION

A heat exchange catheter and method of operation are included in the present invention. The method is adapted to produce hypothermia or hyperthermia in a selected portion of the body without substantially varying the temperature of the remaining portions of the body. The selected body portion will typically be associated with a body conduit which conveys a body fluid to the selected body portion. Of particular interest are the organs of the body which are commonly nourished and maintained by a flow of blood in the arterial system. For example, a flow of blood is introduced to the brain through the carotid artery. Of course the temperature of this blood is usually at the normal body temperature.

By positioning a heat exchange catheter in the body conduit, heat can be added to or removed from the body fluid to heat or cool the selected body portion. For example, the heat exchange catheter can be disposed in the carotid artery where the arterial blood flowing to the brain can be cooled. The flow of cooled blood to the brain reduces the temperature of the brain thereby resulting in cerebral hypothermia. Importantly, this temperature reduction occurs primarily and selectively in the brain; the remaining portions of the body maintain a generally normal body temperature. In accordance with this method, the selected body portion, such as the brain, can be cooled thereby providing the advantages associated with hypothermia for this body portion. The remainder of the body, such as the portions other than the brain, do not experience the reduction in temperature and therefore are not susceptible to the disadvantages of hypothermia. Furthermore, the invention is intended to remotely alter temperature in a region other than the point of introduction into the body, this is different than devices intended for systemic temperature control.

Several factors are of interest in effecting heat transfer in a heat exchanger. These factors include, for example, the convection heat transfer coefficient of the two fluids involved in the heat exchange, as well as the thermal conductivity and thickness of the barrier between the two fluids. Other factors include the relative temperature differential between the fluids, as well as the contact area and residence time of heat transfer. The Reynolds number for each fluid stream affects boundary layers, turbulence and laminar flow.

With concern for these factors, the heat exchange catheter of the present invention includes a shaft having an axis, a fluid inlet lumen and a fluid outlet lumen each extending generally between a proximal end and a distal end of the shaft. A hub disposed at the proximal end provides access to the fluid lumens. At least one balloon is provided in a heat exchange region at the distal end of the shaft, the balloon wall providing the barrier between the two fluids. With the catheter positioned in contact with the body fluid within the conduit, heat transfer occurs across the balloon wall. The relative temperature differential is facilitated with countercurrent flow between the two fluids.

In one aspect of the invention, a first balloon is disposed at the distal end of the shaft and defines with the shaft an inflatable first cavity. Portions of the shaft define a first inlet hole extending in fluid communication between the first lumen and the first cavity. Portions of the shaft define a first outlet hole extending in fluid communication between the first cavity and the fluid outlet lumen. A second balloon disposed relative to the first balloon defines with the shaft an inflatable second cavity with portions of the shaft defining a second inlet hole between the fluid inlet lumen and the second cavity. Portions of the shaft also define a second outlet hole in fluid communication with the second cavity and the fluid outlet lumen. Typically, the first balloon will be disposed distally of the second balloon and the first inlet hole will be larger than the second inlet hole. An elastomeric material covering a valley or volume between the first balloon and the second balloon may be provided to promote mixing necessary for efficient heat exchange yet minimize turbulence and shear which can be damaging to blood.

In an additional aspect of the invention, a method for exchanging heat with a body fluid in a body conduit includes the step of introducing into the body conduit a catheter having an inlet lumen and an outlet lumen. The catheter is provided with a first cavity and a second cavity each in heat transfer relationship with the body fluid in the body conduit.

A heat exchange fluid is introduced into the inlet lumen and through an inlet hole into each of the first cavity and the second cavity. An exchange of heat then occurs between the heat exchange fluid in the first and second cavities and the body fluid in the body conduit. Ultimately, the heat exchange fluid is removed through an outlet hole and the outlet lumen associated with each of the first cavity and the second cavity. Creating non larninar flow in one or both of the heat exchange fluid and the body fluid will improve heat transfer efficiency. Heat transfer can also be effected by various structures which either enhance or inhibit turbulence in the fluids.

These and other features and advantages of the invention will be better understood with a description of the preferred embodiments of the invention and reference to the associated drawings.

DESCRIPTION OF THE DRAWINGS

FIG. 4 is an enlarged axial cross section view of a plurality of balloons disposed in the heat exchange region of the catheter;

FIG. 5 is a radial cross section view of the catheter taken along lines 5—5 of FIG. 4;

FIG. 6 is a radial cross section view similar to FIG. 5 of a further embodiment of the catheter;

FIG. 7 is a perspective view of a further embodiment of the catheter wherein multiple balloons are provided with a longitudinal configuration;

FIG. 8 is a radial cross section view taken along lines 8—8 of FIG. 7;

FIG. 9 is an axial cross section view taken along lines 9—9 of FIG. 7;

FIG. 10 is a perspective view of the catheter illustrated in FIG. 3 further illustrating structures which can facilitate mixing and heat exchange;

FIG. 10A is a perspective view of an embodiment of the catheter having a distal end with a pigtail configuration;

FIG. 10B is a perspective view of the catheter illustrated in FIG. 10A with the distal end straightened by a stylet 174 to facilitate insertion of the catheter;

FIG. 15 is a top plan view of the carotid branch similar to FIG. 13 and showing a further method of operating a heat exchange catheter;

FIG. 16 is a radial cross section of the catheter taken along lines 16—16 of FIG. 15;

DESCRIPTION OF THE PREFERRED EMBODIMENTS AND BEST MODE OF THE INVENTION

Figure 1:
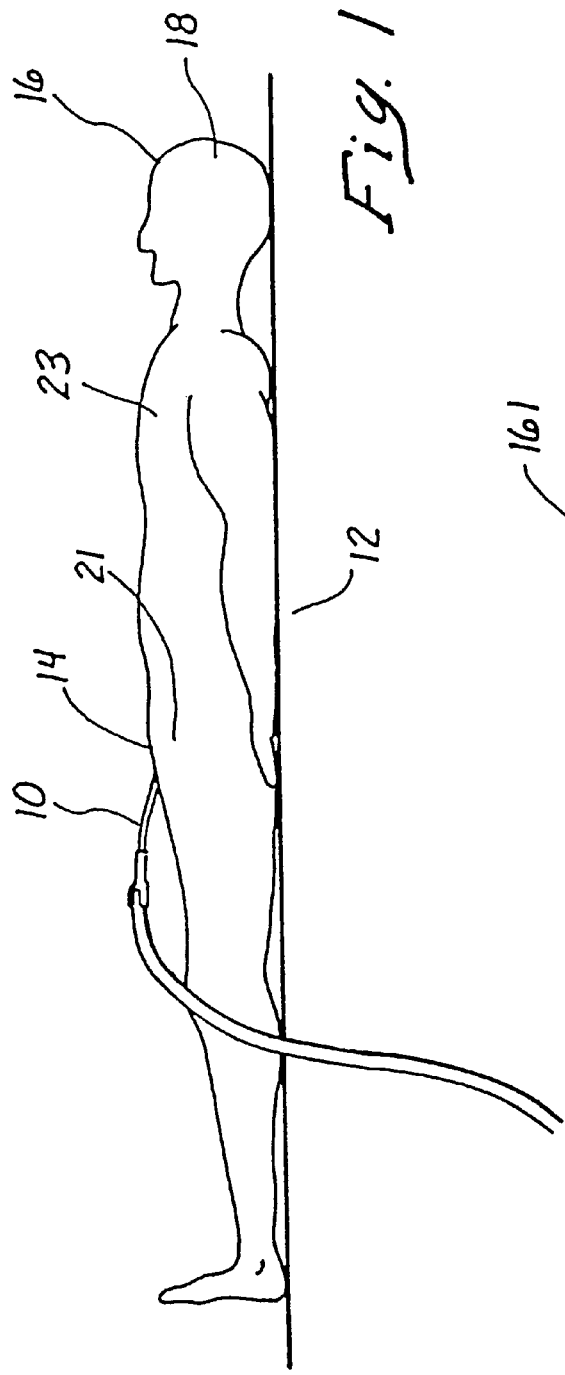
FIG. 1 is side elevation view of a patient lying in a prone position with a heat exchange catheter of the present invention appropriately inserted to facilitate hypothermic treatment of the patient's brain.
Figure 2:
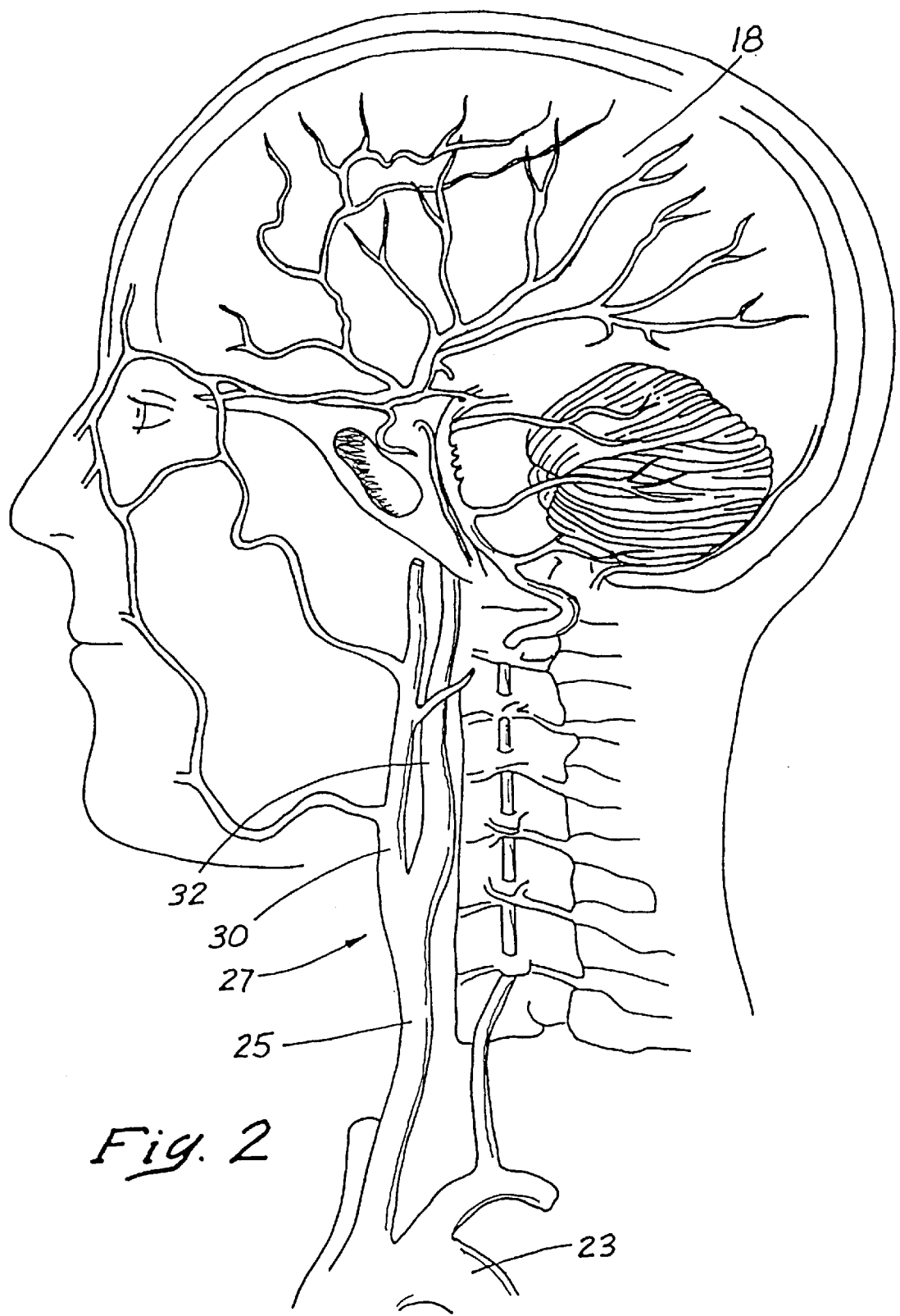
FIG. 2 is an enlarged side elevation view showing the vasculature associated with the patient's head and brain.

A heat exchange catheter is illustrated in FIG. 1 and designated generally by the reference numeral 10. The catheter 10 is operatively disposed with respect to a body 12 of a patient having a groin 14, a head 16, and a brain 18. More specifically, the catheter 10 can be inserted percutaneously through a puncture or surgical cut down at the groin 14, and into the femoral artery 21. Following this initial introduction, the catheter 10 can be moved through the femoral artery 21 and the aortic arch 23, into the common carotid artery 25 best illustrated in FIG. 2. This common carotid artery 25 divides at a carotid branch 27 into an external carotid artery 30, which primarily supplies blood 31 to the face of the patient, and an internal carotid artery 32, which primarily supplies blood to the brain 18 of the patient.

In the concept of this invention, the brain 18 is merely representative of a portion of the body 12 of the patient, and the arteries 21, 25, 30 and 32 are merely representative of conduits which supply a body fluid, such as blood, to a selected portion of the body 12, such as the brain 18. By cooling the body fluid, such as blood 31, in the body conduit, such as the artery 32, the specific body portion, such as the brain 18, can be selectively cooled without significantly affecting the temperature of the remaining portions of the body 12.

Selective hypothermic treatment of the brain 18 is initially of particular interest as it captures the advantages of hypothermia during operative procedures associated with the brain 18 without also capturing the disadvantages of hypothermia with respect to other areas of the body 12. Thus, a surgeon operating to treat an aneurysm in the brain 18, for example, can initially cool the brain 18 in order to facilitate that procedure. This selective hypothermia will be particularly appreciated in those surgical procedures which are primarily directed to the brain 18. Procedures such as stroke, trauma, and other brain related injuries will also benefit up to and during from this selective hypothermia treatment.

Figure 3:
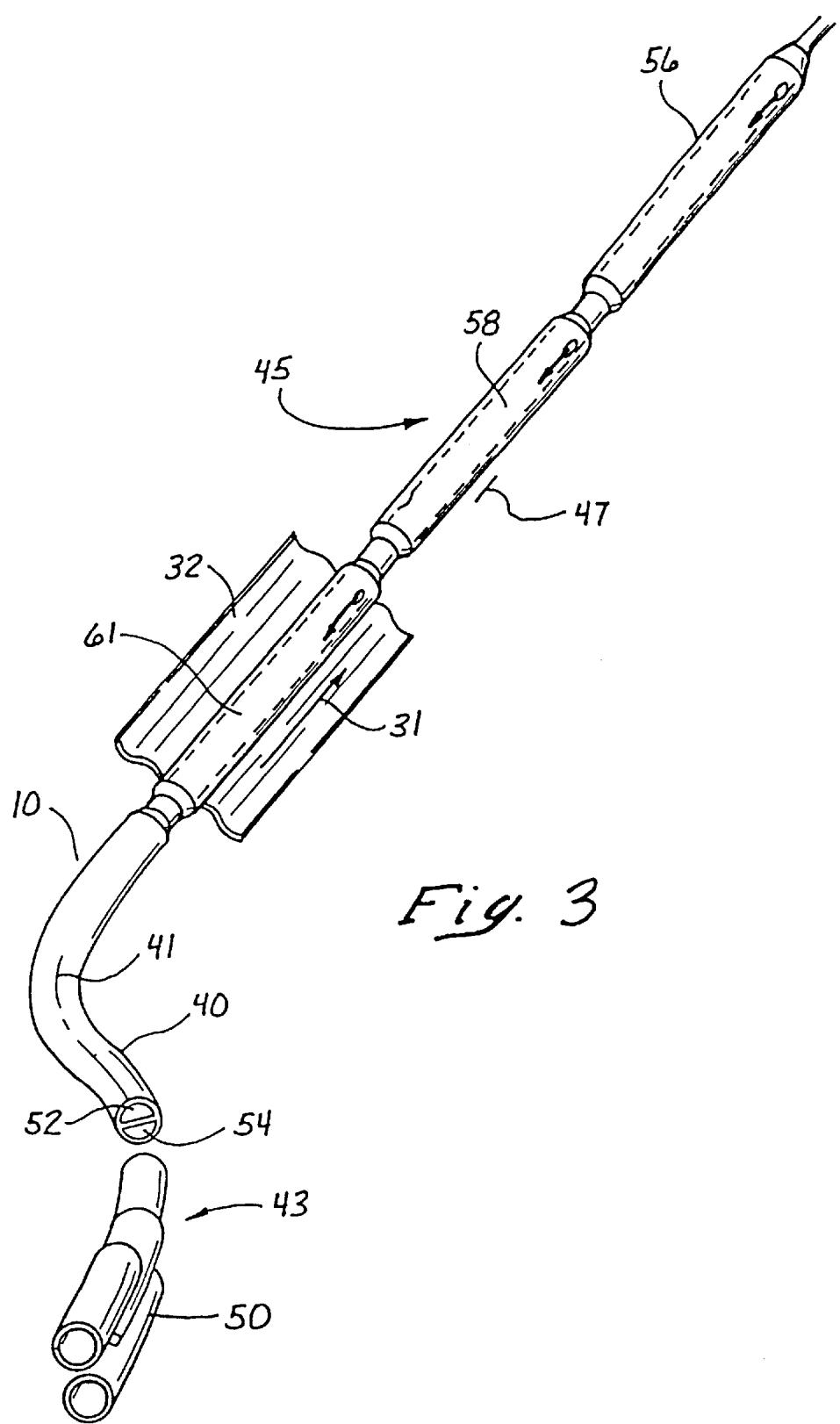
FIG. 3 is a perspective view partially in section of a heat exchange region of the catheter.

A preferred embodiment of the catheter 10 of the present invention is illustrated in FIGS. 3 and 4. From this perspective view, it can be seen that the catheter 10 includes a shaft 40 having an axis 41 which extends between a proximal end 43 and a distal end 45. When operatively disposed, a heat exchange region 47 at the distal end 45 is operatively disposed within the body 12, and a hub 50 at the proximal end 43 is disposed outside of the body 12. Within the shaft 40, a plurality of lumens 52 and 54 extend in fluid communication with the hub 50 and the heat exchange region 47.

A preferred embodiment of the heat exchange region 47 is illustrated in greater detail in FIG. 4 where three balloons 56, 58 and 61 are individually, separately and axially disposed along the shaft 40. It will be appreciated that although the illustrated embodiment includes three balloons, a single balloon or double balloon embodiment may offer further advantages in a particular procedure. All of the balloons 56, 58 and 61 are illustrated to have a significantly larger diameter than the shaft 40. This may not be the case in other embodiments. More specifically, it may be desirable to maximize the dimension of the shaft 40 in order to facilitate flow of the heat exchange fluid. This will also minimize the volume of fluid in the balloon and promote a more rapid heat exchange. In one such embodiment, the diameter of the shaft 40 is in a range between 50 and 90 percent of the diameter of the balloons 56, 58 and 61.

Each of the balloons 56, 58 and 61 can be formed from a piece of sheet material 62, 64 and 66 which is bound or otherwise fixed to the shaft 40 to form a cavity 63, 65 and 67, respectively. An inlet hole 70 provides fluid communication between the lumen 54 and the cavity 63 of the balloon 56. Similar inlet holes 72 and 74 are provided for the balloons 58 and 61. In a like manner, an outlet hole 76 can be formed in the wall of the shaft 40 to provide fluid communication between the lumen 52 and the cavity 63 of the balloon 56. Similar outlet holes 78 and 81 are provided for the balloons 58 and 61, respectively. With this structure, it can be seen that the lumen 54 functions primarily as an inlet lumen for a heat exchange fluid which is illustrated generally as a series of arrows designated by the reference numeral 85.

Initially, the heat exchange fluid 85 is introduced through the hub 50 (FIG. 3) and into the inlet lumen 54. From the lumen 54, the heat exchange fluid 85 passes through the inlet holes 70, 72, 74 and into the respective balloon cavity 63, 65 and 67. The heat exchange fluid 85 then passes into the outlet hole 76, 78, 81 and into the outlet lumen 52 and the hub 50 to regions exterior of the catheter 10.

After the heat exchange fluid 85 is remotely cooled, it is circulated through the balloon cavities 63, 65 and 67 to provide a cold temperature fluid on the inner surface of the sheet materials 62, 64 and 66 which form the walls of the balloons 56, 58 and 61, respectively. With a body fluid, such as blood 31, flowing exteriorly of the balloons 56, 68 and 61, heat transfer occurs across the sheet materials 62, 64 and 66, respectively.

It can be appreciated that this circulation of the heat exchange fluid 85 can be formed with any structure of the shaft 40 which provides two lumens, such as the lumens 52 and 54, each of which can have access to the balloon cavities, such as the cavities 63, 65 and 67. In one embodiment of the shaft 40 illustrated in FIG. 5, a septum 90 is provided which separates the cylindrical shaft 40 into two equally sized lumens 52 and 54. In the embodiment of FIG. 6, the cylindrical shaft 40 is provided with a cylindrical septum 92 which provides the lumen 54 with a circular cross section and the lumen 52 with a moon-shaped cross section. In such an embodiment, the lumen 54 must be defined off-axis from the shaft 40 in order to have access to the balloon cavities, such as the cavity 63.

One of the advantages of a multiple balloon embodiment of the catheter 10 is that the flow and temperature of the heat exchange fluid 85 can be more easily controlled along the entire length of the heat exchange region 47. Realizing that the heat exchange fluid 85 will be coolest prior to entering into a heat exchange with the, blood 31, and warmest after that heat exchange, one can advantageously control not only the velocity and volume of flow, but also the direction of flow within each discrete balloons 56, 58 and 61. Another advantage of a multiple balloon design is the ability of the catheter to bend and flex when placed in a curved vasculature. Single balloon designs would be rigid, stiff and inflexible by comparison.

In order to facilitate the maxinum heat exchange between the fluid 85 and the blood, it is desirable to provide a balanced flow of the heat exchange fluid 85 along the entire length of the heat exchange region 47. In the embodiment illustrated in FIG. 4, efficient heat transfer is facilitated by countercurrent flow where the heat exchange fluid 85 is directed to flow counter to the flow of the blood 31. To that end, the inlet holes 70, 72 and 74 are positioned distally of the outlet holes 76, 78 and 81, respectively. As the blood 31 flows distally along the outer surface of the catheter 10, this relative position of the inlet holes and outlet holes causes the heat exchange fluid to flow in the opposite direction, proximally in each of the balloons 56, 58 and 61.

The amount of flow within each of the balloons 56, 58 and 61 can also be controlled by the size of the inlet holes 70, 72, 74 and outlet holes 76, 78 and 81. In a preferred embodiment, this flow control is provided solely by the inlet holes 70, 72 and 74; the outlet holes 76, 78 and 81 are sized larger than their respective inlet holes so that they offer little resistance to flow. In this embodiment, the inlet holes 70, 72 and 74 are sized to be progressively smaller from the distal end 45 to the proximal end 43. Thus the hole 70 is larger than the hole 72 which is larger than the hole 74. As a result, the resistance to the flow of heat exchange fluid 85 in the most distal balloon 56 is less than that in the most proximal balloon 61. This ensures that the coolest heat exchange fluid 85 is shared equally among all of the balloons 56, 58 and 61 regardless of their position along the shaft 40. In an embodiment wherein the flow is controlled by the outlet holes 76, 78 and 81, these holes can also be provided with a relatively reduced size from the distal end 45 to the proximal end 43. With any of these structures, a more balanced flow of the heat exchange fluid can be achieved in order to facilitate the highest degree of heat exchange along the entire heat exchange region 47. Alternatively, the flow of heat exchange fluid can also be balanced by providing the holes 76, 78 and 81 with non-circular configurations. For example, these holes may be formed as longitudential slits extending axially of the catheter.

A further embodiment of the invention is illustrated in FIG. 7 wherein a single sheet of material 101 is used to form separate and distinct individual balloons, two of which are designated by the reference numerals 103 and 105. As opposed to the radial balloons 56, 58 and 61 of the previous embodiment, the balloons 103 and 105 extend axially along the surface of the shaft 40. For example, the balloons 103 and 105 form individual balloon cavities 107 and 110, respectively, which extend from a distal end 112 to a proximal end 114.

This embodiment of the catheter containing the axial balloons 103 and 105 may include a shaft 40 with a slightly different configuration. As best illustrated in FIG. 9, the shaft 40 may include an outer tube 121 having an outer surface to which the sheet material 101 is attached and within which is disposed a distal sealing plug 123. An inner tube 125, which can be disposed coaxially with the outer tube 121, has an inner lumen 127 and defines with the outer tube 121 an outer lumen 130. A pair of inlet holes 132 and 134 provide flow fluid communication between the inner lumen 127 and the balloon cavities 107 and 110, respectively. Similarly, a pair of outlet holes 136 and 138 provide fluid communication between the balloon cavities 107 and 110 and the outer lumen 130, respectively. An inner plug 141 disposed between the inner tube 125 and outer tube 121 to seal the outer lumen 130 between the inlet holes 132, 134 and outlet holes 136, 138. For the reasons previously noted, a preferred embodiment has inlet holes 132, 134 which are disposed distally of and sized smaller than the outlet holes 136, 138, respectively. This orientation will provide countercurrent flow in a catheter 10 which is inserted downstream into an artery such as the carotid artery 25.

Embodiments which are intended to maximize heat transfer will take advantage of the fact that heat exchange is enhanced when either, or both, the body fluid or the heat exchange fluid is provided with well mixed flow. Mixing can be enhanced by providing irregular surfaces next to which either of these fluids flow. For example, with reference to FIG. 4, it will be noted that a spring 150 can be disposed around the shaft 40 inside each of the balloons, such as the balloon 61. In this embodiment, the spring 150 upsets the lamninar flow of the heat exchange fluid 85 thereby producing the desired mixing of this fluid. Other structures can be positioned within the cavities formed by the balloons 56, 58 and 61.

Mixing can also be enhanced within the body fluid which flows along the outer surface of the catheter 10. In this case, the multiple radial balloon embodiment illustrated in FIG. 4 is of advantage as each of the balloons 56, 58 and 61 represents a peak and defines with the adjacent balloon a valley along which the blood 31 flows. This series of peaks and valleys also upsets the laminar flow of the body fluid. Mixing of the body fluid can also be enhanced by providing other structures along the outer surface of the sheet material 62, 64 and 66 which form the balloons as well as any exposed areas of the shaft 40 in the heat exchange region 47. By way of example, a multiplicity of granules 145 can be adhered to the outer surface of the radial balloons 56, 58 and 61 or the axial balloons 103 and 105 as illustrated in FIG. 9. Ridges can also be provided along these surfaces.

With some body fluids, it may be desirable to inhibit turbulent flow and facilitate laminar flow. This may be true for example in the case of blood where undesirable hemolysis may occur in response to increased turbulence. Such an embodiment might be particularly desirable for use with radial balloons where an outer balloon 152 would promote laminar flow by reducing the height differential between the peaks and valleys defined by the balloons 56, 58 and 61. This outer balloon 152 is best illustrated in FIG. 10. To further promote laminar flow, the outer surface of any structure in the heat exchange region 47 can be provided with a coating 154, such as a hydrophilic or a hydrophobic coating to modify the boundary layer. Thus the outer surface of the shaft 40 as well as the outer surface of any of the balloons 56, 58, 61, 103, 105 and 152 can be provided with the coating 154. The coating 154 may also include other ingredients providing the catheter 10 with additional advantageous properties. For example, the coating 154 may include an antithrombogenic ingredient such as heparin or aspirin. Such a coating 154 would not only inhibit platelet deposition but also the formation of blood clots.

As previously noted, the characteristics of the heat exchange fluid 85 may also be of importance in a particular heat exchange environment. Although the heat exchange fluid 85 may include various liquids, it is believed that gases may provide the greatest temperature differential with the body fluid. Particularly if this fluid includes blood, gases that are inert or otherwise compatible with the vascular system will be appreciated. Although several inert gases might fulfill these requirements, carbon dioxide is used for the heat exchange fluid 85 in a preferred embodiment of the invention.

A further embodiment of the catheter 10 is contemplated for maximizng the surface area available for heat exchange. As illustrated in FIGS. 10A and 10B, the catheter 10 can be formed with a distal end 45 of the shaft 40 disposed in the natural conifiguration of a spiral or pigtail 172. The relatively large diameter of the pigtail 172 facilitates heat exchange, but tends to deter from a low profile desire for insertion. Under these circumstances, it may be advantageous to insert the catheter 10 over a stylet or guidewire 174 in order to straighten the pigtail 172 as illustrated in FIG. 10B.

Figure 11:
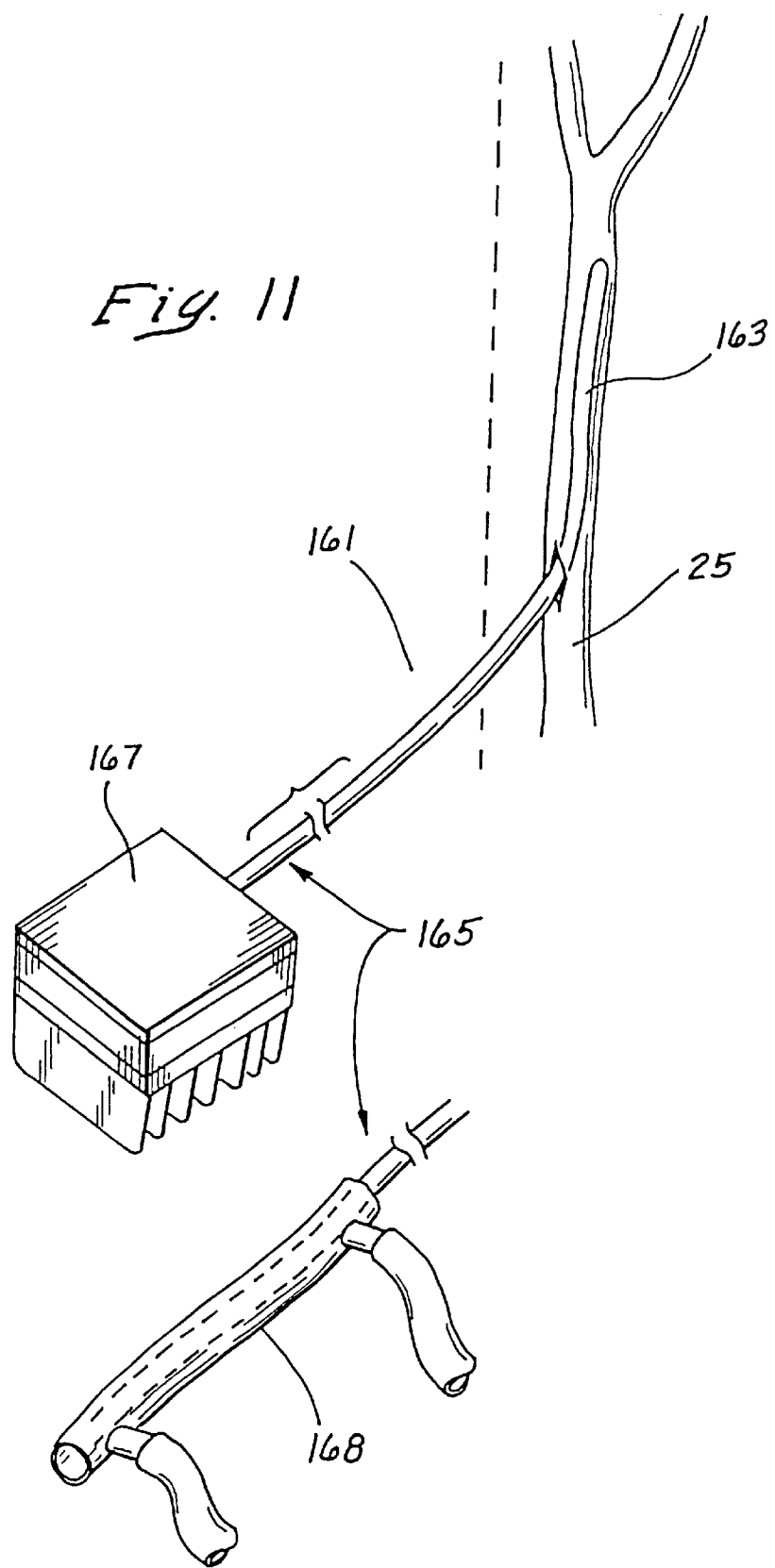
FIG. 11 is a schematic view of an embodiment including a heat pipe.

Hyperthermia and hypothermia for selective regions of the body can also be achieved by placing in the body conduit, such as the carotid artery 25, a heat pipe 161 best illustrated in the schematic view of FIG. 11. In this embodiment, the heat pipe 161 includes a distal end 163 and proximal end 165. The distal end 163 is adapted to be placed within the body conduit, such as the carotid artery 25. The proximal end 165 of the heat pipe 161 is adapted to be connected to an external heat sink or cooler, such as a thermoelectric cooler 167 or water jacket 168. A wick structure 170 is provided in the heat pipe 161 to facilitate a flow of heat exchange fluid from the cooler 167 to the distal end 163.

Figure 12:
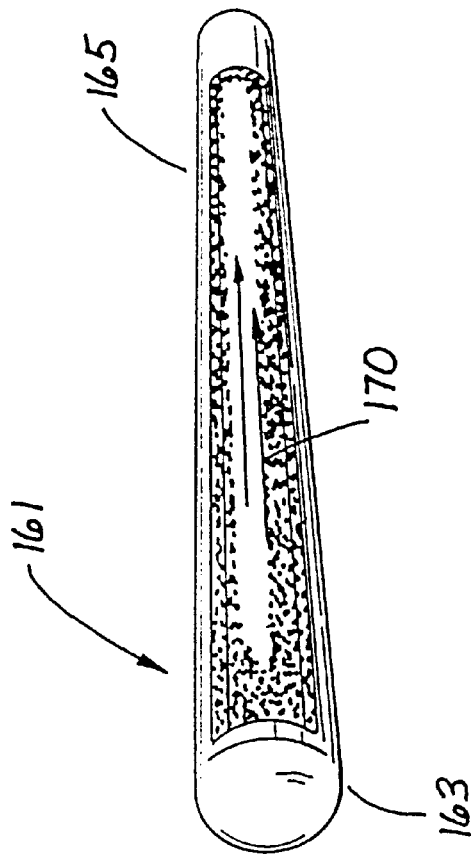
FIG. 12 is a schematic view, partially in section, of a heat pipe adapted for use in the embodiment of FIG. 11.

In a process involving the heat pipe 161, illustrated in FIG. 12, the heat exchange fluid is moved from the proximal end 165 of the heat pipe 161 either by gravity or by capillary action of the wick structure 170 to the distal end 163. At the distal end 163 of the heat pipe 161, heat is transferred from the body fluid, such as blood, to the heat exchange fluid in its liquid state. This heat exchange liquid absorbs a heat of vaporization as it passes into a vapor state in the heat pipe 161. The heat exchange fluid in its vapor state creates a pressure gradient between the ends 163 and 165 of the heat pipe 161. This pressure gradient causes the vapor to flow to the cooler 165 where it is condensed giving up its latent heat of vaporization. The heat exchange fluid in its liquid state then passes back through the heat pipe 161 through the wick structure 170 or by gravity. The passive heat exchange system provided by the heat pipe 161 is vacuum-tight and can be operated with a minimum amount of the heat exchange fluid.

Figure 13:
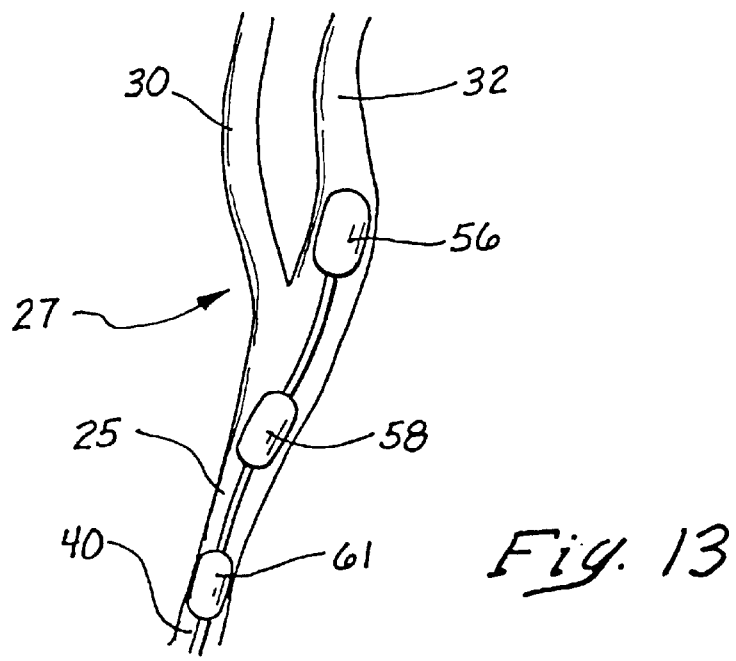
FIG. 13 is a top plan view of carotid artery branch illustrating one method of operation associated with the catheter.

Although the heat exchange catheter 10 will be advantageous in the hyperthermic or hypothermic treatment of any portion of the body 12, it is believed that it will be particularly appreciated in those procedures which can benefit from the hypothermic treatment of the brain 18, such as the treatment of ischemic stroke and/or head trauma. As previously noted in comments directed to FIG. 1, the catheter 10 can be inserted into the femoral artery in the groin 14 and directed through the aortic arch 23 into the common carotid artery 25. As illustrated in FIG. 13, the catheter 10 can then be moved into the region of the arterial branch 27 where it will encounter the external carotid artery 30 and the internal carotid artery 32. Since the external carotid artery 30 is directed primarily to the facial regions, it does not supply a significant amount of blood to the brain 18. In contrast, the internal carotid artery 32 is almost solely responsible for feeding the capillary bed of the brain 18. Based on these considerations, hypothermic treatment of the brain 18 is best addressed by cooling the blood in the internal carotid artery 32 without wasting any of the cooling properties on the external carotid artery 30. In a method associated with one embodiment of the invention, the most distal of the balloons, such as the balloon 56 in FIG. 13 is preferably positioned within the internal carotid artery 32. The more proximal balloons 58 and 61 can be disposed along the common carotid artery 25. This embodiment of the catheter 10 and its associated method will achieve a higher degree of heat transfer within the internal artery 32 than the external artery 30.

Figure 14:
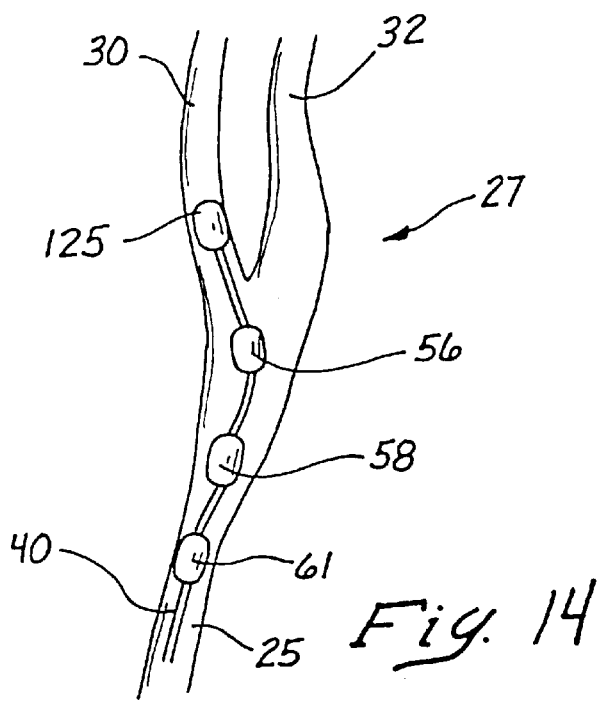
FIG. 14 is a top plan view similar to FIG. 13 and showing a further method of operation with the catheter.

In another embodiment of the catheter 10 best illustrated in FIG. 14, an occlusion balloon 175 is provided distally of the heat exchange region 47. In this embodiment, the occlusion balloon 175 will preferably be inflatable through a separate lumen in the shaft 40. As the catheter 10, approaches the carotid branch 27, the occlusion balloon 81 is directed into the external carotid artery 30 and inflated in order to at least partially occlude that artery. The remaining proximal balloons 56, 58 and 61 in the heat exchange region 47 are left within the common carotid artery 25 to promote heat exchange with the blood flowing to the branch 27. With the external artery 30 at least partially occluded, heat transfer occurs primarily with the blood flowing into the internal carotid artery 32.

A further embodiment of the invention is illustrated in FIG. 15 operatively disposed in the common carotid artery 25 and internal carotid artery 32. In this case, the catheter 10 includes a balloon 181 which is attached to the distal end of the shaft 40. In this case, the balloon 181 is provided with a spiral configuration. More specifically, the balloon 181 may be formed from several individual balloons, as with the embodiment of FIG. 7, for as individual flutes 183 on the single balloon 181. In either case, the separate balloons (such as the balloons 103, 105 of FIG. 7) or the flutes 183 are oriented in a spiral configuration around the axis 41 of the catheter 10. The shaft 40 can be provided with any of the configurations previously discussed such as the accentric configuration of FIG. 6.

By providing the balloon 181 with a spiral configuration, heat exchange is enhanced by at least two of the factors previously discussed. Notably, the surface area of contact is increased between the blood 31 flowing externally of the balloon 181 and the heat exchange fluid flowing internally of the balloon 181. The spiral configuration also enhances the mixing properties of both the blood 31 and the heat exchange fluid 85.

As noted, the heat exchange fluid 85 may be cooled to a sub-zero temperature such as −18° C. In order to thermally protect the internal lining of the artery 32 from direct contact with the sub-zero coolant, it may be desirable to provide the tips of the flutes 183 with a thicker wall 185, as shown in FIG. 16. This thicker wall 185 might be advantageous in any of the balloon configurations previously discussed, but would appear to be most advantageous in the embodiments of FIG. 7 and 15 where the contact with the artery 32 tends to be more localized by the longitutudal balloons 103, 105 (FIG. 7) on the spiral flutes 183 (FIG. 15).

Figure 17:
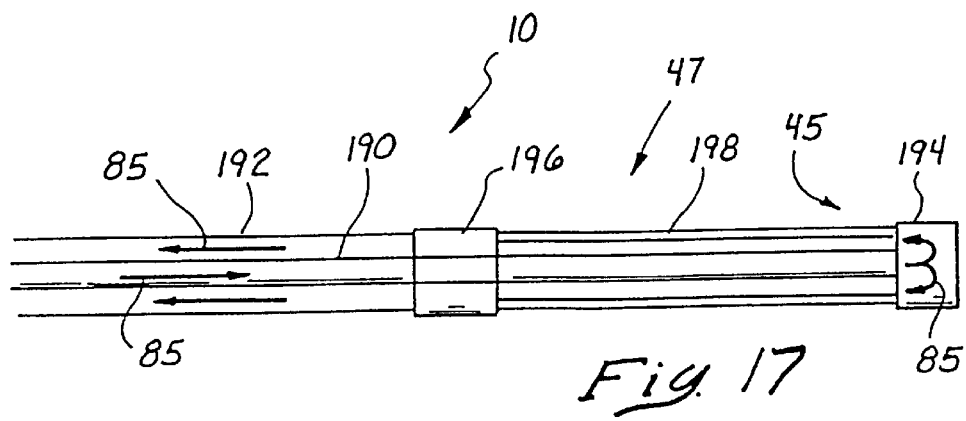
FIG. 17 is an axial cross section view of a further embodiment of the invention including hollow fibers in the heat exchange region.

Still a further embodiment of the invention is illustrated in FIG. 17. In this embodiment, the shaft 40 includes an inner tube 190 disposed within an outer tube 192. These tubes 190, 192 may be concentric and longitutingly movable relative to each other. The tubes 190, 192 terminate respectively in manifolds 194, 196. Between these manifolds 194, 196, a multiplicity of hollow fibers 198 can be disposed at the distal end 45 to define the heat exchange region 47 of the catheter 10. The hollow fibers 198 each include an internal lumen which provides fluid communication between the manifolds 194 and 196. In operation, the heat exchange fluid 85 flows distally along the inner tube 190 into the distal manifold 194. From this manifold 194, the heat exchange fluid 85 flows into the internal lumens of the hollow fibers 198 proximally to the proximal manifold 196. The warmer heat exchange fluid 85 flows proximally from the manifold 196 between the inner tube 190 and outer tube 192.

The hollow fibers 198 offer several advantages to this embodiment of the catheter 10. Notably, they provide a very high surface area between the blood 31 and the heat exchange fluid 85. This greatly enhances the heat exchange characteristics of this embodiment. Countercurrent flow can also be maintained further facilitating the heat exchange capabilities of this catheter.

Figure 18:
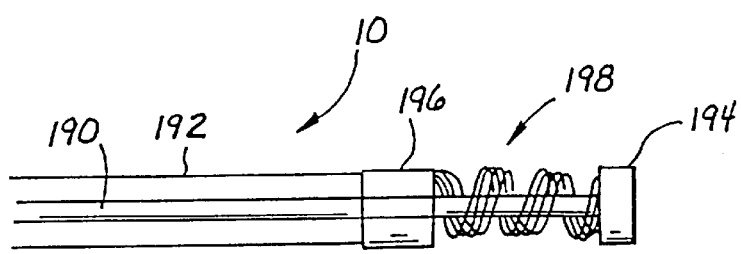
FIG. 18 is a side elevation view similar to FIG. 17 and illustrating the hollow fibers in a compacted configuration.
Figure 19:
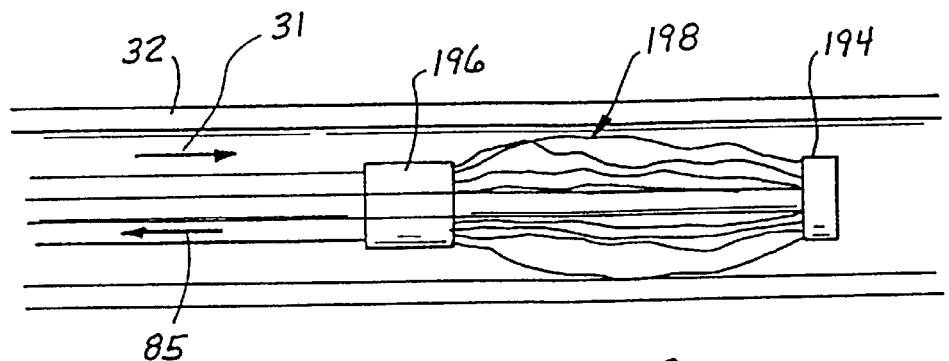
FIG. 19 is an axial cross section view of the catheter of FIG. 17 operatively disposed and configured to permit the hollow fibers to float and undulate within a blood stream.

The hollow fibers 198 can be spiraled as illustrated in FIG. 18 by twisting the inner tube 190 with respect to the outer tube 192. This characteristic can be used to provide a shorter and lower profile heat exchange region 47 in order to facilitate introduction of the catheter 10. A lower profile may also be obtained by separating the manifolds 194 and 197 a distance substantially equal to the length of the fibers 198. This will tend to hold the fibers in a straight, parallel relationship and thereby facilitate introduction of the catheter 10. The spiraled configuration of the hollow fibers 198 can be maintained during heat exchange in order to further increase the heat exchange area per unit length of the catheter 10. Alternatively, the fibers 198 can be positioned to loosely float and undulate between the manifolds 194 and 196 as illustrated in FIG. 19. This characteristic of the fibers 198 will not only provide the increased heat exchange area desired, but also promote mixing within the blood 31.

Generally speaking with respect to any of the balloon embodiments previously discussed, it will be appreciated that the advantages of this invention can be derived with respect to a single balloon. On the other hand, there seem to be several advantages associated with multiple balloon embodiments. Notably, a more even and balanced transfer of heat exchange can be achieved with multiple balloons. In addition, there appears to be better mixing with respect to both the blood 31 as well as the heat exchange fluid 85. Multiple balloons also provide an increased surface area relative to single balloon embodiments. Furthermore, the overall flexibility of the catheter 10 is enhanced with multiple balloons separated by interruptions which provide natural flex points for the catheter. When the balloons experience the high perfusion pressure, they become more stiff. The reduced diameter interruptions provide for increased flexibility at these joints.

Additional flexibility can be derived by providing the shaft 40 with variable stiffness. This variability can be produced by different materials forming the shaft 40 along its length or alteratively, tapering or otherwise varying the diameter of the shaft 40. For example, the shaft 40 can be progressively tampered from its proximal end 43 to its distal end 45 in order to provide a softer and more flexible heat exchange region 47.

With the intent of maximizing heat transfer with the body fluid in a conduit feeding a specific region of the body, any of the factors previously noted can be addressed to provide structural modifications to the foregoing embodiments. Of course changes in the material or size of any of the structural elements described can be varied to achieve various heat exchange properties. Realizing the many changes which might be contemplated, one is cautioned not to limit this concept only to the specific embodiments illustrated and disclosed, but rather to determine the scope of the invention with reference to the following claims.

What is claimed is:

1. A catheter adapted to be disposed in a body conduit to facilitate an exchange of heat between the catheter and a body fluid flowing in the body conduit, comprising:

a shaft having an axis, a first lumen, and a second lumen each extending generally between a proximal end and a distal end of the shaft;

a first sheet material disposed to define a first cavity exteriorly of the shaft;

a second sheet material disposed to define a second cavity exteriorly of the shaft;

portions of the shaft defining separate inlet holes providing fluid communication between the first lumen and each of the first cavity and the second cavity;

portions of the shaft defining separate outlet holes providing fluid communication between the second lumen and each of the first cavity and the second cavity; whereby a heat exchange fluid can be introduced into the first lumen and through the inlet and outlet holes to and from the first and second cavities to facilitate the exchange of heat with the body fluid flowing in the body conduit.

2. The catheter recited in claim 1 wherein the body conduit is a vessel and the body fluid is blood.

3. The catheter recited in claim 2 wherein the vessel is an artery and the catheter is adapted to be operatively positioned in the artery with the blood flowing distally along the distal end of the catheter.

4. The catheter recited in claim 3 wherein the inlet hole is disposed distally of the outlet hole in the first cavity.

5. The catheter recited in claim 4 wherein the inlet hole associated with the first cavity is larger than the inlet hole associated with the second cavity.

6. The catheter recited in claim 2 wherein the vessel is a vein and the catheter is adapted to be operatively positioned within the vein with the blood flowing proximally along distal end of the catheter.

7. The catheter recited in claim 6 wherein the inlet hole is disposed proximally of the outlet hole in the first cavity.

8. The catheter recited in claim 7 wherein the inlet hole associated with the first cavity is larger than the inlet hole associated with the second cavity.

9. The catheter recited in claim 1 wherein the first cavity is formed by a first balloon extending circumferentially of the shaft;

the second cavity is formed by a second balloon extending circumferentially of the shaft distally of the first balloon.

10. A method for exchanging heat with a body fluid in a body conduit, comprising the steps of:

introducing into the body conduit a catheter having an inlet lumen and an outlet lumen;

providing the catheter with a first cavity and a second cavity in heat transfer relationship with the body fluid in the body conduit;

introducing a heat exchange fluid into the inlet lumen through an inlet hole and into the first cavity;

exchanging heat between the heat exchange fluid and the body fluid in the body conduit; and removing the heat exchange fluid from each of the first cavity and the second cavity through an outlet hole and the outlet lumen.

11. The method recited in claim 10 wherein the introducing step includes the step of introducing the catheter into the body conduit in the direction of flow of the body fluid.

12. The method recited in claim 10 wherein the body conduit is an artery and the body fluid is blood.

13. The method recited in claim 10 wherein the introducing step includes the step of introducing the catheter into the body conduit against the direction of flow of the body fluid.

14. The method recited in claim 13 wherein the providing step includes the step of positioning the inlet hole proximally of the outlet hole.

15. The method recited in claim 10 wherein the providing step includes the step of forming the outlet hole larger than the inlet hole.

16. The method recited in claim 10 wherein the providing step includes the step of positioning the outlet hole proximal of the inlet hole.

17. The method recited in claim 10 wherein the providing step further comprises the step of positioning a first balloon exteriorly of the inlet lumen and the outlet lumen to form the first cavity.

18. The method recited in claim 17 wherein the providing step further comprises the steps of:

positioning a second balloon exteriorly of the inlet lumen and the outlet lumen to form the second cavity; and positioning a third balloon to cover the first balloon and the second balloon.

19. The method recited in claim 10 wherein the step of exchanging heat includes the step of withdrawing heat from the body fluid to cool the body fluid.

* * * * *

UNITED STATES PATENT AND TRADEMARK OFFICE
CERTIFICATE OF CORRECTION

PATENT NO.    : 6,416,533 B1                                                    Page 1 of 1
DATED         : July 9, 2002
INVENTOR(S)   : Yves Pierre Gobin, Scott Evans, Mike Jones and Wayne Noda It is certified that error appears in the above-identified patent and that said Letters Patent is hereby corrected as shown below:

Drawings,
Figure 4, correct the lead line of reference number 74 to lead to the inlet hole
Figure 9, add -- label reference number 141 and lead line to the inner plug --
Fig. 14, (Sheet 8 of 19), correct label "125" to -- 175 --

Column 9,
Line 3, correct the text "the occlusion balloon 81" to -- the occlusion balloon 175 --

Signed and Sealed this

Twenty-sixth Day of November, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO. : 6,416,533 B1 Page 1 of 1
APPLICATION NO. : 09/546814
DATED : July 9, 2002
INVENTOR(S) : Gobin et al.

It is certified that error appears in the above-identified patent and that said Letters Patent is hereby corrected as shown below:

On the cover page item (73) city of assignee The Regents of the University of California, "Berkeley", should read --Oakland--.

Signed and Sealed this

Sixth Day of July, 2010

David J. Kappos
*Director of the United States Patent and Trademark Office*